US009029336B2

(12) United States Patent
Liddle et al.

(10) Patent No.: US 9,029,336 B2
(45) Date of Patent: *May 12, 2015

(54) XENOBIOTIC RELATED INDUCTION OF GENE EXPRESSION

(75) Inventors: Christopher Liddle, Chatswood (AU); Bryan James Goodwin, Carrborro, NC (US)

(73) Assignee: The University of Sydney, Sydney (AU)

( * ) Notice: Subject to any disclaimer, the term of this patent is extended or adjusted under 35 U.S.C. 154(b) by 0 days.

This patent is subject to a terminal disclaimer.

(21) Appl. No.: 12/629,186

(22) Filed: Dec. 2, 2009

(65) Prior Publication Data

US 2010/0146652 A1    Jun. 10, 2010

Related U.S. Application Data

(63) Continuation of application No. 11/324,921, filed on Jan. 4, 2006, now Pat. No. 7,638,614, which is a continuation of application No. 09/700,991, filed as application No. PCT/AU99/00381 on May 20, 1999, now Pat. No. 6,984,489.

(30) Foreign Application Priority Data

May 20, 1998   (AU) ........................................ PP3628

(51) Int. Cl.
A61K 48/00   (2006.01)
C12N 5/00    (2006.01)
C12Q 1/68    (2006.01)

(52) U.S. Cl.
CPC ....... C12Q 1/6897 (2013.01); *A01K 2267/0393* (2013.01)

(58) Field of Classification Search
CPC .................................................. C12N 310/15
USPC .......................................... 514/44 R; 435/325
See application file for complete search history.

(56) References Cited

U.S. PATENT DOCUMENTS

| 4,997,757 A | 3/1991 | Schiestl |
| 5,429,948 A | 7/1995 | Crespi et al. |
| 5,849,998 A | 12/1998 | Gottesman et al. |
| 6,432,639 B1 | 8/2002 | Lichter et al. |
| 2002/0138855 A1 | 9/2002 | Zhang et al. |
| 2002/0145341 A1 | 10/2002 | Corbett, Jr. et al. |
| 2002/0150915 A1 | 10/2002 | Berkenstam et al. |

FOREIGN PATENT DOCUMENTS

| EP | 644267 | 3/1995 |
| EP | 1 206 906 | 5/2002 |
| WO | WO99/13106 | 3/1999 |
| WO | WO99/35246 | 3/1999 |
| WO | WO99/48915 | 9/1999 |
| WO | WO99/61622 | 12/1999 |
| WO | WO01/11951 | 2/2001 |
| WO | WO01/20025 | 3/2001 |
| WO | WO01/20026 | 3/2001 |
| WO | WO01/79845 | 10/2001 |
| WO | WO02/08451 | 1/2002 |
| WO | WO02/25270 | 3/2002 |
| WO | WO02/36784 | 5/2002 |
| WO | WO02/083897 | 10/2002 |
| WO | WO02/088305 | 11/2002 |

OTHER PUBLICATIONS

Vanrompay et al. (2000) Serology of *Chlamydiaceae psittaci* infections in psittaciformes by use of a recombinant enzyme-linked immunosorbent assay: Recombinant DNA technology at work. Seminars in Avian and Exotic Pet Medicine 9(1): 43-49.*
Granvil at al, "Expression of the human CYP3A4 gene in the small intestine of transgenic mice: in vitro metabolism and pharmacokinetics of midazolam", Drug Metabolism and Dispostion, vol. 31, No. 5, May 1, 2003, pp. 548-558.
Zhang et al. "A transgenic mouse model with a luciferase reporter for studying in vivo transcriptional regulation of the human CYP3A4 gene", Drug Metabolism and Disposition, vol. 21, No. 8, Aug. 1, 2003, pp. 1054-1064.
Hamzeiy H et al. "Mutation analysis of the human CYP3A4 gene 5' regulatory region: population screening using non-radioactive SSCP". Mutation Research. 500(1-2): 103-110 (Mar. 20, 2002).
Pascussi J M et al. "Evidence for the presence of a functional pregnane X receptor response element in the CYP3A7 promoter gene" Biochemical and Biophysical Research Communications 260(2):377-381 (1999).
Reid J M et al., "Rat and human liver cytochrome P-450 isoform metabolism of ecteinascidin 743 does not predict gender-dependent toxicity in humans," Clin. Cancer Res. 8(9):2952-2962, (Sep. 2002).
Martinez C et al., "Expression of paclitaxel-inactivating CYP3A activity in human colorectal cancer: implications for drug therapy," Br. J Cancer 87(6):681-686, (Sep. 2002).
Zhang W et al, "Differential regulation of the human CYP3A4 promoter in transgenic mice and rats." Drug Metabolism and Disposition, 32(2): 163-167 (Feb. 2004).
Birren et al.: "Mus musculus cloneRP23-161k8, low pass sequence sampling" XP002382554 retrieved from EBI Database accession No. AC111090. [Online] May 27, 2004.
Herrmann J et al, "Comparative analysis of adenoviral transgene delivery via tail or portal vein into rat liver" Arch Virol, 149(8):1611-1617 (Aug. 2004).
Xie et al. "Reciprocal activation of Xenobiotic response genes by nuclear receptors SXR/PXR and CAR" *Genes and Development*, 14:3014-3023 (2000).
Ledirac et al. "Effects of macrolide antiobiotics on CYP3A expression in human and rat hepatocytes interspecies differences in response to Troleandomycin" *Drug Metabolism and Disposition* 28(12):1391-1393 (2000).

(Continued)

*Primary Examiner* — Peter Paras, Jr.
*Assistant Examiner* — Magdalene Sgagias
(74) *Attorney, Agent, or Firm* — Husch Blackwell LLP

(57) ABSTRACT

An isolated nucleic acid molecule comprising a nucleotide sequence encoding a transcriptional enhancer of cytochrome P450 (P450) CYP3A4 production or expression, and uses of the nucleic acid molecule for screening compounds for xenobiotic induction of CYP3A4 expression in cells and animals.

7 Claims, 6 Drawing Sheets

(56) References Cited

OTHER PUBLICATIONS

Pascussi et al. "Dexamethasone enhances constitutive androstane receptor expression in human hepatocytes : consequences on cytochrome P450 gene regulation" *Molecular Pharmacology*, 58(6):1441-1450 (2000).
Yanagida A et al. "A novel cis-acting DNA element required for a high level of inducible expression of the rat P-450c gene." *Mol Cell Biol*, 10(4):1470-1475 (1990).
Gonzalez F J et al. "Human P450PCN1: sequence, chromosome localization, and direct evidence through cDNA expression that P450PCN1 is nifedipine oxidase." DNA (1988) 7(2): 79-86.
Gellner K et al: "Genomic Organization of the Human Cyp3a Locus: Identification of a New, Inducible Cyp3a Gene" *Pharmacogenetics*,11(2):111-121 (Mar. 2001).
Toide K et al: "Gene structure of mouse Cyp3aII: Evidence for an enhancer element within its 5' flanking sequences" *Archives of Biochemistry and Biophysics, 338 1* • 43-49 (1997).
Itoh S et al: "Isolation of a promoter region in mouse cytochrome P450 3A (Cyp3A16) gene and its transcriptional control" *Biochimica Et Biophysica ACTA*, 1350(2):155-158 (1997).
Finta C et al. "The human cytochrome P450 3A locus. Gene evolution by capture of downstream exons", *Gene* 260(1-2):13-23 (2000).
MacGregor et al. "New molecular endpoints and methods for routine toxicity testing," *Fundamental and Applied Toxicology* 26(2):156-173 (1995).
Smith et al., "Molecular genetics of the human cytochrome P450 monooxygenase superfamily," *Xenobiotica* 28(12):1129-1165 (1998).
Yanagimoto et al., "Mouse liver cytochrome P-450 (P-450111AM1): its cDNA cloning and inducibility by dexamethasone," *Biochim. Biophys. Acta* 1130(3):329-332 (1992).
Geick A et al. "Nuclear receptor response elements mediate induction of intestinal MDR1 by rifampin." The Journal of Biological Chemistry 276(18):14581-71Epubi(Jan. 31, 2001).
Quattrochi et al., "CYP3A regulation: from pharmacology to nuclear receptors," *Drug Metabolism and Disposition* 29(5):615-622, May 2001.
Montoliu L, Gene transfer strategies in animal transgenesis, Cloning and Stem Cells, 4(11:39-46 (Mar. 2002).
Houdebine LM "The methods to generate transgenic animals and to control transgene expression" J Biotechnology 98:145-160 (2002).
Genbank Accession No. D28565.
Genbank Accession No. AF280107.
Ristevski S, "Making Better Transgenic Models: Conditional, Temporal, and Spatial Approaches" Molecular Biotechnology, 29:153-164 (2005).
Smith K R, "Gene transfer in higher animals: theoretical considerations and key concepts", *Journal of Biotechnology*, 99(1):1-22 (Oct. 9, 2002).
Robertson G R et al. "Transgenic mouse models of human CYP3A4 gene regulation", *Molecular Pharmacology*, 640:42-50 (2003).
Hashimoto et al., *Eur, J. Biochem* 218:585-595 (1993).
Dogra et al., *Clinical and Experimental PharmacoloancPhysiology*, 25:1-9 (Jan. 1998).
Kolars et al., *Pharmacogenetics*, 4:247-259 (1994).
Kovaleva et al., *Biochem, Biophys. Res. Comm.*, 221:129-132 (1996).
Ogg et al., *Eur. J. of Drug Metabolism and Pharmacoldnetics*, 22(4):331-313 (1997).
Hakkela et al., *Crit. Rev Toxicol.* 28(1)35-72 (Jan. 1998).
Gonzalez et al., *Mot. Cell Biol.*, 10:1470-1475 (1990): DNA, 7:79-86 (1988); and Genbank Accession No. D1131.
J.M. Lehmann et al., "The Human Orphan Nuclear Receptor PXR is Activated by Compounds that Regulate CYP3A4 Gene Expression and Cause Drug Interactions,"..1. *Clin. Invest.*, 102(5)1016-1023 (1998).
G. Betilsson et al., identification of a Human Nuclear Receptor Defines a New Signaling Pathway for CYP3A Gene Expression and Cause Drug Interactions, *Proc. Nat'l Acad. Sci., USA*, 95;12208-12213 (Oct. 1998).

Blumberg et al., "SXR, A Novel Steroid and Xenobiotic Sensing Nuclear Receptor," *Genes & Dev.*, 12:3195-3205 (1998).
D.J. Mangelsdorf et al., "The Nuclear Receptor Superfamily: The Second Decade," *Cell*, 83:835-839 (Dec. 1995).
M. Baes et al., "A New Orphan Member of the Nuclear Hormone Receptor Superfamily that Interacts with a Subset of Retinoic Acid Response Elements," *Mol. Cell Biol.*, 14: 1544-15521Mar. 1994).
T.R. Rebbeck et al., "Modification of the Clinical Presentation of Prostate Tumors by a Novel Genetic Variant in CYP3A4," *J. Nat'l Cancer Inst.*, 90(16):1225-1229 (Aug. 1998).
C.A. Felix et al., "Association of CYP3A4 Genotype with Treatment-Related Leukemia," *Proc. Nat'l Acad. Sci. USA*, 95:13176-13181 (Oct. 1998).
Goodwin et al., *Mot. Pharmacol.*, 56:1329-1339 (1999).
Barwick et al. Trans-species gene transfer for analysis of glucocorticoid-inducible transcriptional activation of transiently expressed human CYP3A4 and rabbit CYP3A6 in primary cultures of adult rat and rabbit hepatocytes.
Lawn et al. The isolation and characterization of linked delta- and beta-globin genes from a cloned library of human DNA. *Cell* (1978) 15: 1157-1174.
Zilliacus et al. Modulation of DNA-binding specificity within the nuclear receptor family by substitutions at a single amino acid position. *Proteins*. (1995) 21(1):57-67.
Fougerousse et al. Human-mouse differences in the embryonic expression patterns of developmental control genes and disease genes. *Human Molecular Genetics* (2000) 9(4):659.
Valerio et al. Activity of the adenosine deaminase promoter in transgenic mice. *Nucleic Acids Research* (1988) 16:10083-10097.
Ramsden et al. Phenobarbital induction and tissue-specific expression of the rat CYP2B2 gene in transgenic mice. *Journal of Biological Chemistry* (1993) 268(29):21722-6.
Jones et al. Induction of the Cyp1 a-1 dioxin-responsive enhancer in transgenic mice. *Nucleic Acids Research* (1991) 19(23):6547-51.
Campbell et al. Regulation of the CYP1A1 promoter in transgenic mice: an exquisitely sensitive on-off system for cell specific gene regulation. Journal of Cell Science (1996) 109(11):2619-25.
Komori et al. Transgenic Drosophila carrying mammalian cytochrome P-4501A1: an application to toxicology testing. *Carcinogenesis* (1993) 14(8):1683-8.
Kliewer et al. An orphan nuclear receptor activated by pregnanes defines a novel steroid signaling pathway. Cell (1998) 92(1):73-82.
Wolf et al. Use of transgenic animals in understanding molecular mechanisms of toxicity. *Journal of Pharmacy and Pharmacology*. (1998) 50(6):567-74.
Ogg et al. A reporter gene assay to assess the molecular mechanisms of xenobiotic-dependent induction of the human CYP3A4 gene in vitro. Xenobiotica. 1999 29(3):26979.
Bertilsson, et al., Functionally Conserved Xenobiotic Responsive Enhancer in Cytochrome P 450 3A7, Biochemical and Biophysical Research Communications 280, 139-144 (2001).
Olsen A K, Hansen K T, Friis C. "Pig hepatocytes as an in vitro model to study the regulation of human CYP3A4: prediction of drug-drug interactions with 17 alpha-ethynylestradiol." Chem Biol Interact 107(1-2):93-108 (1997).
Achira M et al, "Comparative studies to determine the selective inhibitors for p-glycoprotein and cytochrome P4503A4." AAPS Pharmsci [Electronic Resource]. 199, 1(4):F18 1-F18 6 (1999).
Ahern H. "Biochemical, reagent kits offer scientists good return on investment." The Scientist 9(15):20 (Jul. 1995).
Goodwin B et al. Genbank Accession No. AF185589.
Martin D I K and Whitelaw E. The vagaries of variegating transgenes. *Bioessays* 18:919-923 (1996).
Robertson, G et al. Position-dependent variegation of globin transgene expression in mice. *Proc. Natl. Acad. Sci. USA* 92:5371-5375 (1995).
Robertson, G et al. Age dependent silencing of globin transgenes in the mouse. *Nucleic Acids Research* 24:1465-1471 (1996).
Dobie K W et al. Variegated transgene expression in mouse mammary gland is determined by the transgene integration locus. *Proc. Natl. Acad. Sci. USA* 93:6659-6664 (1996).

(56) References Cited

OTHER PUBLICATIONS

Elliot J et al. Random activation of a transgene under control of a hybrid hCD2 locus control region/Ig enhancer regulatory element. *EMBO J.* 14:575-584 1995).
Henikoff S Conspiracy of silence amongst repeated transgenes. *Bioessays* 20:532-535 (1998).
Garrick D et al. Repeat-induced gene silencing in mammals. *Nature Genetics* 18:56-59 (1998).
Jones S A et al. The pregnane X receptor: a promiscuous xenobiotic receptor that has diverged during evolution. *MoL Endocrinol.* 14:27-39 (2000).
Wei et al. The nuclear receptor CAR mediates specific xenobiotic induction of drug metabolism. *Nature* 407(6806):920-923 (2000).
Xie W et al. Humanized xenobiotic response in mice expressing nuclear receptor SXR. *Nature* 406(6794):435-9 (2000).
Smith, T.F. and Waterman M.S. "Comparison of biosequences" (1981) Ad. *Appl. Math.*, 2:482-489.
Needleman, S.B. and Wunsch, C.D. "A general method applicable to the search for similarities in the amino acid sequence of two proteins." (1970) *J. Mol. Biol.* 48(3):443-453.
Kamataki T. et al. "Preclinical approach for identifying drug interactions." Cancer Chemother Pharmacol 42 Suppl: S50-3 (1998).
International Search Report related to PCT/AU99/00381.
Chu-Sien et al. "Promoter analysis of the nuclear gene encoding the chloroplast glyceraldehyde-3-phosphate dehydrogenase B subunit of Arabidopsis" Plant Mol. Bio 46:131-141 (2001).
Omilli et al. "Sequences involved in initiation of simian virus 40 late transcription in the absence of T antigen" Mol. and Cell. Bio. Jun. 1986, 1875-1885.
Pietrzkowski et al. "Characterization of an enhancer-like structure in the promoter region of the proliferating cell nuclear antigen (PCNA) gene" Exp. Cell. Res. 193:283-293 (1991).
Genbank Accession No. D11131.1.
Lawn et al. "The isolation and characterization of linked δ- andβ-globin genes from a cloned library of human DNA" Cell, vol. 15, 1157-1174, Dec. 1978, MIT.
Leninger et al., Part III Bioenergetic and Metabolism, 1993, p. 780.
Mangelsdorf et al., The Nuclear Receptor Superfamily: The Second Decade, Cell, vol. 83, 835-839, Dec. 15, 1995.
Bertilsson et al., Identification of a human nuclear receptor defines a new signaling pathway for CYP3A induction, Proc. Natl. Acad. Sci. USA vol. 95, pp. 12208-12213, Oct. 1998.
Blumberg et al., SXR, a novel steroid and xenobiotic-sensing nuclear receptor, downloaded from www.genesdev.org on Dec. 5, 2007, p. 3195-3205.

\* cited by examiner

TCTAGAGAGA TGGTTCATTC CTTTCATTTG ATTATCAAAG AAACTCATGT CCCAATTAAA    60

GGTCATAAAG CCCAGTTTGT AAACTGAGAT GATCTCAGCT GAATGAACTT GCTGACCCTC   120

TGCTTTCCTC CAGCCTCTCG GTGCCCTTGA AATCATGTCG GTTCAAGCAG CCTCATGAGG   180

CATTACAAAG TTTAATTATT TCAGTGATTA TTAAACCTTG TCCTGTGTTG ACCCCAGGTG   240

AATCACAAGC TGAACTTCTG ACAAGAACAA GCTATCATAT TCTTTTCAAT TACAGAAAAA   300

AGTAAGTTAA TTGATAGGAT TTTTTTTGTT TAAAAAAAAT GTTACTAGTT TTTGAAAAGG   360

TAATATGTTG CACATGGTAA ACACTAAGAA GGTATAAGAG CATAATGCTT TTATACTACT   420

AAGAATAATG TTTTCTCTAA GTTTTTTTTG GTAGATGCTT TCATCAGATT AAGAAAATTC   480

CCTGCTATTA GTTGTTGAAG GTTTTTATAT CATAAATGAA AGTTGAATAT TATTATCATA   540

TATTATTAAT ATATTGTTAT TGAACTATCA AAGCCTTTTC CTAAAACCAT TGAGATGATC   600

TTATAACCAT TCTCCTTTAA CCTGTTGACG AG                                 632

Figure 1

```
                        SEQUENCE LISTING

<160> NUMBER OF SEQ ID NOS: 11

<210> SEQ ID NO 1
<211> LENGTH: 632
<212> TYPE: DNA
<213> ORGANISM: Homo sapiens

<400> SEQUENCE: 1
tctagagaga tggttcattc ctttcatttg attatcaaag aaactcatgt cccaattaaa      60
ggtcataaag cccagtttgt aaactgagat gatctcagct gaatgaactt gctgaccctc     120
tgctttcctc cagcctctcg gtgcccttga aatcatgtcg gttcaagcag cctcatgagg     180
cattacaaag tttaattatt tcagtgatta ttaaaccttg tcctgtgttg accccaggtg     240
aatcacaagc tgaacttctg acaagaacaa gctatcatat tcttttcaat tacagaaaaa     300
agtaagttaa ttgataggat ttttttttgtt taaaaaaaat gttactagtt tttgaaaagg     360
taatatgttg cacatggtaa acactaagaa ggtataagag cataatgctt ttatactact     420
aagaataatg ttttctctaa gttttttttg gtagatgctt tcatcagatt aagaaaattc     480
cctgctatta gttgttgaag gtttttatat cataaatgaa agttgaatat tattatcata     540
tattattaat atattgttat tgaactatca aagccttttc ctaaaaccat tgagatgatc     600
ttataaccat tctcctttaa cctgttgacg ag                                   632

<210> SEQ ID NO 2
<211> LENGTH: 21
<212> TYPE: DNA
<213> ORGANISM: Homo sapiens

<400> SEQUENCE: 2
gaatgaactt gctgaccctc t                                                21

<210> SEQ ID NO 3
<211> LENGTH: 24
<212> TYPE: DNA
<213> ORGANISM: Homo sapiens

<400> SEQUENCE: 3
ccttgaaatc atgtcggttc aagc                                             24

<210> SEQ ID NO 4
<211> LENGTH: 24
<212> TYPE: DNA
<213> ORGANISM: Homo sapiens

<400> SEQUENCE: 4
aggtgaatca caagctgaac ttct                                             24

<210> SEQ ID NO 5
<211> LENGTH: 21
<212> TYPE: DNA
<213> ORGANISM: Homo sapiens

<400> SEQUENCE: 5
atatattgtt attgaactat c                                                21

<210> SEQ ID NO 6
```

```
<211> LENGTH: 24
<212> TYPE: DNA
<213> ORGANISM: Homo sapiens

<400> SEQUENCE: 6
atatgaactc aaaggaggtc agtg                                            24

<210> SEQ ID NO 7
<211> LENGTH: 21
<212> TYPE: DNA
<213> ORGANISM: Homo sapiens

<400> SEQUENCE: 7
agatgaactt catgaactgt c                                               21

<210> SEQ ID NO 8
<211> LENGTH: 14
<212> TYPE: DNA
<213> ORGANISM: Homo sapiens
<220> FEATURE:
<221> NAME/KEY: misc_feature
<222> LOCATION: (7)..(9)
<223> OTHER INFORMATION: n is a, c, g, or t

<400> SEQUENCE: 8
tgaactnnnt gacc                                                       14

<210> SEQ ID NO 9
<211> LENGTH: 18
<212> TYPE: DNA
<213> ORGANISM: Homo sapiens
<220> FEATURE:
<221> NAME/KEY: misc_feature
<222> LOCATION: (7)..(12)
<223> OTHER INFORMATION: n is a, c, g, or t

<400> SEQUENCE: 9
tgaaatnnnn nnggttca                                                   18

<210> SEQ ID NO 10
<211> LENGTH: 18
<212> TYPE: DNA
<213> ORGANISM: Homo sapiens
<220> FEATURE:
<221> NAME/KEY: misc_feature
<222> LOCATION: (7)..(12)
<223> OTHER INFORMATION: n is a, c, g, or t

<400> SEQUENCE: 10
tgaatcnnnn nntgaact                                                   18

<210> SEQ ID NO 11
<211> LENGTH: 15
<212> TYPE: DNA
<213> ORGANISM: Homo sapiens
<220> FEATURE:
<221> NAME/KEY: misc_feature
<222> LOCATION: (7)..(9)
<223> OTHER INFORMATION: n is a, c, g, or t

<400> SEQUENCE: 11
tattgtnnnt gaact                                                      15
```

XENOBIOTIC RELATED INDUCTION OF GENE EXPRESSION

TECHNICAL FIELD

The present invention relates to modulating or effecting gene expression and/or formation of human and non-human animal cytochrome P450 CYP3A subfamily enzymes.

BACKGROUND ART

Development of therapeutic drugs for medical and veterinary use is important in order to improve and advance treatment modalities in humans and animals. Unfortunately, many drugs that are developed and subsequently used have been found to have limited half lives in vivo due to rapid metabolism by the recipient. It would be advantageous to have a system for screening potential new drugs for susceptibility to metabolic action in patients.

A cytochrome P450 (P450) termed CYP3A4 is an important human gene that codes for an enzyme expressed in the liver, and to a lesser extent a range of other tissues. It is quantitatively the most abundant P450 in human liver. The CYP3A4 enzyme is pivotal to the metabolism of many exogenous chemicals (xenobiotics), including therapeutic drugs, as well as a range of endogenous compounds, such as steroid hormones. Changes in the level of expression of CYP3A4 can dramatically affect the rate of elimination of therapeutic drugs and thus impact on their effectiveness. A range of exogenous chemicals, including some therapeutic drugs, (hereafter termed 'xenobiotic inducers') are able to increase the transcriptional rate of the CYP3A4 gene and hence the formation of the CYP3A4 enzyme. The result is the elimination of drugs metabolised by CYP3A4 being greatly increased thereby diminishing their therapeutic effect.

The present inventors have obtained a DNA molecule, lying approximately 7.5 kilobases 5' to the transcription initiation site of the human P450 CYP3A4 gene, that is responsible for the transcriptional induction of the CYP3A4 gene by xenobiotic inducers, including therapeutic drugs and is also involved in the constitutive expression of this gene. This nucleic acid molecule, called a 'xenobiotic-responsive enhancer module' (XREM) by the present inventors, has a number of beneficial uses.

DISCLOSURE OF INVENTION

In a first aspect, the present invention consists in an isolated nucleic acid molecule including a nucleotide sequence forming a transcriptional enhancer of cytochrome P450 (P450) CYP3A4 production or expression.

Preferably, the isolated nucleic acid molecule includes a nucleotide sequence substantially as shown in FIG. 1 (SEQ ID NO: 1), or a functionally equivalent nucleotide sequence or portion thereof encoding an enhancer of CYP3A4, or a sequence which hybridises to the nucleotide sequence of FIG. 1 (SEQ ID NO: 1), or a sequence which shows at least 60% homology with the nucleotide sequence of FIG. 1 (SEQ ID NO: 1). More preferably, the nucleic acid molecule has at least 80% homology with the nucleotide sequence of FIG. 1 (SEQ ID NO: 1) and most preferably the nucleic acid molecule has at least 90% homology with that sequence.

In a preferred embodiment, the present invention consists in an isolated nucleic acid molecule including nuclear receptor response elements from the 5'-flanking region of CYP3A4. Preferably, the response elements are selected from XREM-DR3-1 GAA TGAACTTGC TGACCC TCT (SEQ ID NO: 2); XREM-ER6 CCT TGAAAT CATGTG GGTTCA AGC (SEQ ID NO: 3); XREM-DR6 AGG TGAATC ACAAGC TGAACT TCT (SEQ ID NO: 4); XREM-DR3-2 ATA TATTGT TAT TGAACT ATC (SEQ ID NO: 5); and Prox-ER6 ATA TGAACT CAAAGG AGGTCA GTG (SEQ ID NO: 6).

As a number of specific response elements have been identified in the enhancer of CYP3A4 by the present inventors, it will be appreciated that SEQ ID NO: 1 can be used to identify other response elements. As the full sequence of the enhancer is not necessary for subsequent use, the present invention includes within its scope the use of response elements from the enhancer with intermediate or connecting sequences from other sources.

Preferably, the isolated nucleic acid molecule has a nucleotide sequence substantially as shown in FIG. 1 (SEQ ID NO: 1).

In a preferred form, the CYP3A4 is human CYP3A4. It will be appreciated, however, that the present invention also includes other human CYP3A subfamily enzymes and CYP3A subfamily enzymes from non-human animals.

The induction of CYP3A4 is preferably by one or more xenobiotic inducers.

The present invention also includes polynucleotides which hybridise to the sequence shown in FIG. 1 (SEQ ID NO: 1). Preferably, the polynucleotide hybridises to the sequence set out in FIG. 1 (SEQ ID NO: 1) under high stringency. As used herein, stringent conditions are those that (a) employ low ionic strength and high temperature for washing, for example, 0.015 M NaCl/0.0015 M sodium citrate/0.1% NaDodSO$_4$ at 50° C.; (b) employ during hybridisation a denaturing agent such as formamide, for example, 50% (vol/vol) formamide with 0.1% bovine serum albumin, 0.1% Ficoll, 0.1% polyvinylpyrrolidone, 50 mM sodium phosphate buffer at pH 6.5 with 750 mM NaCl, 75 mM sodium citrate at 42° C.; or (c) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 g/ml), 0.1% SDS and 10% dextran sulfate at 42° C. in 0.2×SSC and 0.1% SDS.

In a further preferred embodiment of the first aspect of the present invention, the polynucleotide capable of hybridising to the nucleotide sequence of FIG. 1 (SEQ ID NO: 1) is less than 5000 nucleotides, however, it can be less than 1000 or even less than 500 nucleotides in length. Preferably, the hybridising polynucleotides are at least 10, more preferably at least 18 nucleotides in length.

In a second aspect, the present invention consists in a genetic construct suitable for use in measuring the induction of a reporter gene, the construct including a nucleic acid molecule according to the first aspect of the present invention operably linked to a nucleic acid molecule encoding a reporter molecule.

Preferably, the nucleic acid molecule encoding the reporter molecule encodes an enzyme. The nucleic acid molecule encoding the reporter may encode the enzyme CYP3A4 or a functionally equivalent enzyme. Examples of suitable reporter molecules include firefly luciferase, beta-galactosidase, chloramphenicol acetyltransferase, alkaline phosphatase and green fluorescent protein. Alternatively, the nucleic acid may encode a messenger RNA (mRNA) that can be detected by standard techniques such as northern blotting or ribonuclease protection assays.

It will be appreciated, however, that the nucleic acid molecule encoding the reporter molecule may be any nucleic acid molecule or gene that, when expressed, has a detectable activity. The nucleic acid molecule encoding reporter molecule does not have to be associated with the cytochrome P450 system although the inducer of transcription (XREM) used is derived from that gene system. It will also be appreciated that the nucleic acid molecule encoding the reporter gene may include more than one reporter molecule.

In a third aspect, the present invention consists in an assay system including the construct according to the second aspect of the present invention such that on exposure of the system to a xenobiotic inducer, expression of the nucleic acid molecule encoding the reporter molecule is enhanced.

The assay system includes within its scope cells containing the construct (XREM) and cell-free systems capable of supporting the function of the construct (XREM). Such cell-free systems typically contain cell extracts, such as nuclear extracts, but not always. The assay system also includes experimental systems that determine binding of compounds to the construct (XREM). These include DNase I footprinting and gel-retardation assays. These assay systems can be used to detect activation of the construct (XREM), but are not as convenient for mass screening of compounds as the reporter gene constructs. Preferably, the enhanced expression results in an increase in the activity of the reporter gene product.

The cell may be any suitable cell including bacterial, plant or animal cells. The construct may exist as a separate genetic entity in the cell or be incorporated into the genome of the cell. Furthermore, the cell may form part of a transgenic animal.

In a fourth aspect, the present invention consists in a method for screening a compound for xenobiotic induction of CYP3A4 expression in a cell, the method including exposing an assay system according to the third aspect of the present invention to the compound and measuring for the induction or the potential for expression of the nucleic acid molecule encoding the reporter molecule.

The method according to the present invention is particularly suitable for screening new therapeutic drugs. Although there may be many potential drugs available at the developmental stage, if a drug induces CYP3A4 expression in vivo then its suitability as an effective therapeutic agent is reduced. In use, the drug's half life will be shorter due to being metabolised by the induced CYP3A4 enzyme in the liver of a patient. Another problem that can arise is that the drug causes the enhanced metabolism or elimination of other drugs given to the patient. Drug "cocktails" or combinations of drugs are often required to treat many diseases. If one of the drugs administered has the propensity to enhance the clearance of one or more other drugs used in the treatment of a particular disease, then this is highly undesirable and may result in the reduced efficacy of the treatment.

It will be appreciated that if a compound or new drug fails to induce the expression of the reporter gene when tested by the method according to the present invention, then this is an indication that the compound or new drug may not be an xenobiotic inducer and therefore a suitable candidate for further development. A screening process would be beneficial in therapeutic drug development as unsuitable candidates may be disregarded at an early of stage of development. Furthermore, alternate or related chemical compounds may also be developed based on a compound's negative result in the screening assay.

The method may also include exposing a transgenic animal and measuring in the animal for induction of the reporter gene after exposure to the chemical or drug.

In a fifth aspect, the present invention consists in the XREM according to the first aspect of the present invention as a genetic analysis tool. In this respect, mutations responding to allelic variants in humans are introduced and their functional consequences observed. Also, as the XREM has a defined function of transcriptional regulation it can be used for the determination of allelic variation.

In a further aspect, the use involves the determination of allelic variation within the XREM (relevant to constitutive expression) and the use of site directed mutation of the XREM to determine the impact of allelic variation.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

In order that the present invention may be more clearly understood, preferred forms will be described with reference to the following examples and drawings.

BRIEF DESCRIPTION OF DRAWINGS

FIG. 1 shows a sequence of the XREM region of the CYP3A4 gene. Base numbering is relative and does not indicate location within the CYP3A4 gene structure.

MODES FOR CARRYING OUT THE INVENTION

Definitions

General Molecular Biology

Figure 2:
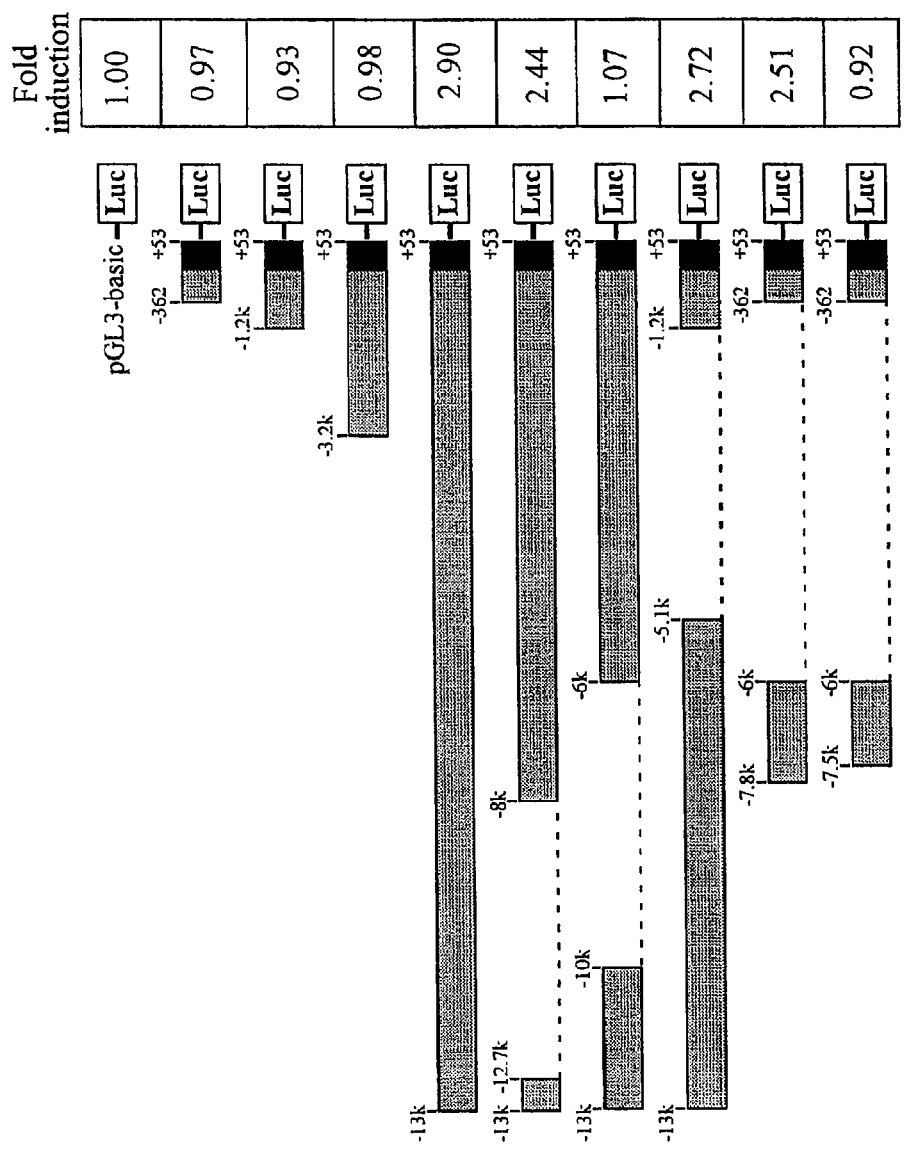
FIG. 2 shows an example of a series of deletion constructs of the 5'-flanking region of the CYP3A4 gene used to define xenobiotic-responsive elements. Fold induction of luciferase reporter gene expression refers to treatment with a potent CYP3A4 inducer (5 µM rifampicin) compared to vehicle alone (0.1% dimethyl sulphoxide). This was normalised to the activity of an 'empty' pGL3-basic reporter vector. All constructs were temporarily transfected into HepG2 cells.

Unless otherwise indicated, the recombinant DNA techniques utilised in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (Editors), Current Protocols in Molecular Biology, Greene Pub. Associates and Wiley-Interscience (1988, including all updates until present) and are incorporated herein by reference.

Mutants, Variants and Homology—Nucleic Acids

Mutant polynucleotides will possess one or more mutations which are deletions, insertions, or substitutions of nucleotide residues. Mutants can be either naturally occurring (that is to say, isolated from a natural source) or synthetic (for example, by performing site-directed mutagensis on the DNA). It is thus apparent that polynucleotides of the invention can be either naturally occurring or recombinant (that is to say prepared using recombinant DNA techniques).

An allelic variant will be a variant that is naturally occurring within an individual organism.

Nucleotide sequences are homologous if they are related by divergence from a common ancestor. Consequently, a species homologue of the polynucleotide will be the equivalent polynucleotide which occurs naturally in another species. Within any one species a homologue may exist as numerous allelic variants, and these will be considered homologues of the polynucleotide. Allelic variants and species homologues can be obtained by following standard techniques known to those skilled in the art. Preferred species homologues include those obtained from representatives of the same Phylum, more preferably the same Class and even more preferably the same Order.

A polynucleotide at least 70% identical, as determined by methods well known to those skilled in the art (for example, the method described by Smith, T. F. and Waterman, M. S. (1981) Ad. Appl. Math., 2: 482-489, or Needleman, S. B. and Wunsch, C. D. (1970) J. Mol. Biol., 48: 443-453), to the that of the present invention are included in the invention, as are proteins at least 80% or 90% and more preferably at least 95% identical to the polynucleotide of the present invention. This will generally be over a region of at least 60, preferably at least 90, contiguous nucleotide residues.

Substantially Purified

By "substantially purified" the present inventors mean a polynucleotide that has been separated from lipids, nucleic acids, other polypeptides or polynucleotides, and other contaminating molecules.

Active Fragment

By "active fragment" the present inventors mean a fragment of a sequence shown in FIG. 1 which encodes a transcriptional enhancer of cytochrome P450 (P450) termed CYP3A4

BACKGROUND

Human Cytochrome P450 3A4 (CYP3A4)

CYP3A4 is an important gene in human clinical pharmacology. In addition to it's pivotal role in the metabolism of therapeutic drugs and endogenous steroid hormones, recent studies have associated a non-coding polymorphisms in a putative regulatory region of this gene with both prostate cancer and the development of secondary leukaemia after cancer chemotherapy. An understanding of CYP3A4 gene regulation is important in the development of therapeutic drugs. In addition, CYP3A4 gene represents a novel target for pharmacological manipulation and a tool for both pharmacogenetic analysis and possibly disease prediction. However, a thorough understanding of CYP3A4 regulation and genetics is required to achieve these goals. This present invention is directed to a regulatory module within the 5'-flanking region of the CYP3A4 gene that is responsible for it's xenobiotic induction and constitutive expression.

Human Hepatic Cytochromes P450s

The human hepatic P450s are membrane bound haemoproteins active in the metabolism of a broad range of lipophilic substrates. P450 proteins are of considerable relevance to medicine, not only because of their central role in drug and other xenobiotic metabolism, but also because of their many 'natural' or 'endogenous' lipophilic substrates. These include steroid hormones, fatty acids (especially leukotrienes), cholesterol, and bile salts. It is considered likely that the P450 system evolved because of its pivotal role in cholesterol and steroid metabolism. A small subset of constitutively expressed human hepatic P450s, including CYP3A4, are of particular interest because they are quantitatively the most important forms and catalyse a range of biologically important reactions.

Physiological Role Acid Variability of CYP3A4

CYP3A4, the predominant cytochrome P450 found in human liver, comprises up to 60% of the total amount of hepatic cytochrome P450 protein. CYP3A4 is involved in the metabolism of an extensive range of drugs and endogenous steroids. It has been estimated that in excess of 60% of all therapeutic drugs are metabolised in full or in part by this enzyme. Changes in the level of expression of CYP3A4 can have a dramatic impact on the metabolism of therapeutic drugs and thus cause a number of important drug interactions. Also, the variable level of constitutive expression of this enzyme makes a major contribution to the inter-individual variability of oxidative drug metabolism. In addition, CYP3A4 is the major pathway of oxidative metabolism of steroid hormones, catalysing the 6β-hydroxylation of several endogenous steroids such as cortisol, androstenedione and testosterone as well as the 2- and 4-hydroxylation of estradiol to form catachol estrogens. Two other CYP3A subfamily cytochromes P450 are found in man. CYP3A7 is mainly found in foetal liver while CYP3A5 is found mainly in adult liver as well as the lungs and kidneys.

Regulation of CYP3A4 Gene Expression

CYP3A4 is subject to multiple levels of transcriptional regulation. These include xenobiotic induction (for example, by some therapeutic drugs), tissue-specific regulation, as well as substantial variability in constitutive expression (up to 10-fold between individuals not exposed to known inducers or inhibitors).

Xenobiotic Induction of CYP3A Genes

CYP3A genes in several mammalian species, including man, are transcriptionally-inducible by a number of structurally dissimilar therapeutic drugs. Working on the assumption that xenobiotic induction of CYP3A4 is mediated by a response element in the 5'-flanking region of this gene, the present inventors went on to clone 22 kilobases (kb) of the CYP3A4 gene 5' to the transcription initiation site. This was used to generate a deletion series of constructs covering 13 kb of the 5'-flanking region that were linked to a luciferase reporter gene for analysis of transcriptional activity. These constructs were temporarily transfected into a human hepatoblastoma cell line (HepG2) as well as primary cultures of rat and rabbit hepatocytes. By comparing transfected cells treated with inducing agents, such as rifampicin, to untreated controls, the present inventors have determined that the response element [termed hereafter a xenobiotic-responsive enhancer module (XREM)] is approximately located between −7.2 kb and −7.8 kb 5' to the transcription initiation site (FIG. 2). The present studies show the XREM to be a complex element spanning several hundred base pairs (FIG. 1, SEQ ID NO: 1). DNase I footprinting further shows that this region is rich in DNA-protein interactions and appears capable of binding several transcription factors of which the recently described human pregnane-X receptor (hPXR) (the pregnane-X receptor is identical to the pregnane-activated receptor (PAR) and the steroid-X receptor (SXR)) [1-3] is the most important for xenobiotic-induced regulation of CYP3A4.

Figure 3:
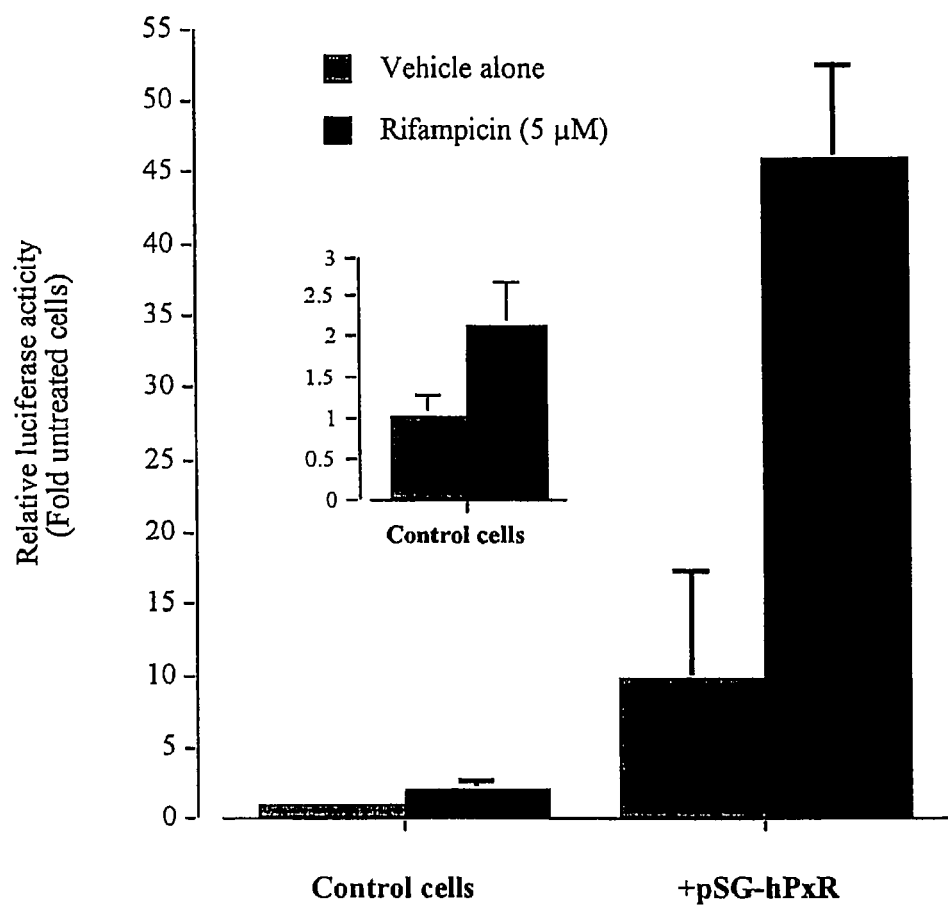
FIG. 3 shows the effect of cotransfection of a hPXR expression vector (pSG-hPxR) on HepG2 cells containing an CYP3A4 XREM reporter construct, in the presence or absence of a potent CYP3A4 inducer (5.mu.M rifampicin). The insert shows a magnified view of the effects on the control cells.

The present inventors have demonstrated that the hPXR forms the vital link between the xenobiotic inducer (eg, rifampicin) and elements within the XREM. In humans, rifampicin treatment typically induces the expression of the CYP3A4 gene 50-fold or more. When a suitable reporter construct containing the XREM sequence is transfected into HepG2 cells, rifampicin treatment results in a 3- to 5-fold induction of reporter gene expression. However, the present inventors have demonstrated that co-transfection of the XREM-containing reporter gene construct with a hPXR expression vector restores full rifampicin induction (FIG. 3). The present inventors have also shown that other drugs, such as phenobarbitone and clotrimazole also act on the XREM via the hPXR (FIG. 4), demonstrating that this is a general mechanism for xenobiotic induction of the CYP3A4 gene.

Figure 5:
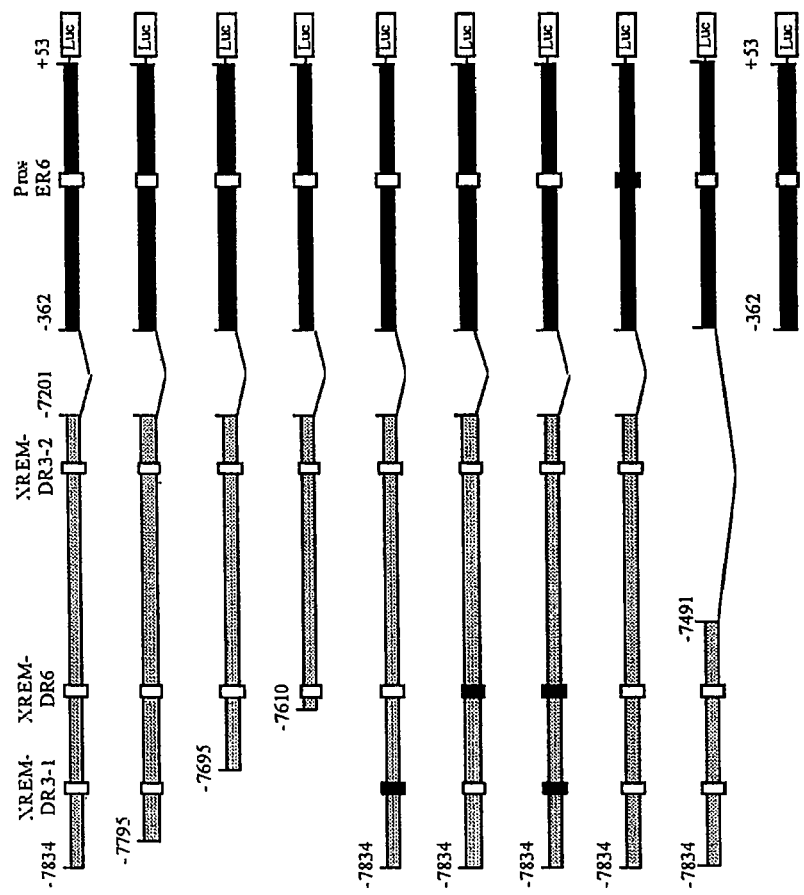
FIG. 5 shows the effect of deletions and site-directed mutagenesis of putative nuclear receptor response elements on the transcriptional induction of the CYP3A4 5'-flanking region by 5 µM rifampicin. Filled in boxes correspond to mutated elements. Numbering is relative to the transcription initiation site.

The hPXR is an orphan nuclear receptor, belonging to the nuclear receptor gene superfamily [4]. Studies from other laboratories suggest that it binds to DNA as a heterodimer with the retinoid-X receptor (RXR) [1-3]. The present inventors have identified several putative nuclear receptor response elements within the XREM arranged as direct repeats with a 3 base spacer (DR3), direct repeats with a 6 base spacer (DR6) or everted repeats with a 6 base spacer (ER6) (Table 1). In order to evaluate the affinity of these putative response elements for HPXR-RXR heterodimers, electromobility shift assays (EMSA) were performed using with in-vitro transcribed/translated hPXR and RXR. These showed that XREM-DR3-1 and Prox-ER6 efficiently bind hPXR-RXR heterodimers resulting in a gel-shift, but no shift was apparent with XREM-DR6 and XREM-DR3-2. Despite this result, the present inventors have shown by site-directed mutagenesis experiments that the latter two response are functionally important (FIG. 5). The XREM-ER6 did bind hPXR-RXR heterodimers, but with less affinity than the XREM-DR3-1 or Prox-ER6.

TABLE 1

Sequences of putative nuclear receptor response elements within the CYP3A4 XREM compared to a putative response element in the proximal CYP3A4 5'-flanking region (Prox-ER6). An element from the proximal 5'-flanking region of the rat CYP3A23 gene (CYP3A23 DR3) that interacts with the pregnane-X receptor is shown for comparison purposes.

| Designation | Sequence (Core Spacer Core) | | | SEQ ID |
|---|---|---|---|---|
| XREM-DR3-1 | gaa TGAACT | tgc | TGACCC tct | 2 |
| XREM-ER6 | cct TGAAAT | catgtc | GGTTCA agc | 3 |
| XREM-DR6 | agg TGAATC | acaagc | TGAACT tct | 4 |
| XREM-DR3-2 | ata TATTGT | tat' | TGAACT atc | 5 |
| Prox-ER6 | ata TGAACT | caaagg | AGGTCA gtg | 6 |
| CYP3A23 DR3 | aga TGAACT | tca | TGAACT gtc | 7 |

(Note:
The core motifs are shown in bold. DR3 is a 3 base spacer while DR6 and ER6 are both 6 base spacers.)

When the XREM is deleted from reporter gene constructs containing the CYP3A4 5'-flanking region, no xenobiotic-inducible activity is seen, demonstrating that the XREM region is essential for the process of xenobiotic induction. Moreover, when the XREM is linked to a heterologous gene promoter, such as a minimal herpes simplex virus thymidine kinase promoter, xenobiotic induction is observed, demonstrating that the XREM is not absolutely reliant on other elements within the CYP3A4 gene. However, for maximal xenobiotic responsiveness, the present inventors have determined that an ER6 element within the proximal promoter region of the CYP3A4 gene (Prox-ER6, Table 1) is required. It is important to appreciate that the Prox-ER6 element has no xenobiotic-inducible activity in the absence of the XREM.

Figure 6:
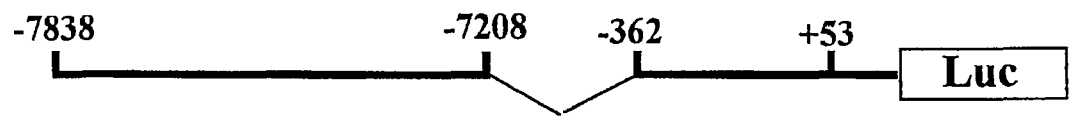
FIG. 6 shows an optimised CYP3A4 5'-flanking region construct coupled to a luciferase reporter gene (Luc) for determining the ability of xenobiotics to induce transcriptional activation of the CYP3A4 gene. Numbering is relative to the transcription initiation site.

From the above findings, an optimised DNA sequence for the analysis of the xenobiotic induction of the CYP3A4 gene has been determined. It includes the XREM region as well as bases −356 to +53 of the proximal CYP3A4 promoter and is termed construct #5 (FIG. 6). Typically, this DNA sequence is linked to a reporter gene and studied in a suitable cell or cell-free system. The present inventors have determined that the HepG2 cell line cultured in Dulbecco's Modified Eagle's Medium (DMEM) with 10% foetal bovine serum, transfected using a commercially available reagent (FuGene-6, Boehringer Mannheim, Mannheim, Germany) performs well.

Tissue-Specific and Constitutive Expression of CYP3A Subfamily Genes

The mechanisms determining the tissue-restricted and constitutive expression of CYP3A4 are probably similar, if not the same. Understanding these aspects of gene regulation are critical to a definitive explanation of why humans exhibit such marked inter-individual variability in CYP3A4-mediated drug metabolism.

Human CYP3A subfamily P450s are predominantly expressed in the liver. However, there is significant tissue-restricted extrahepatic expression. CYP3A4 is expressed in significant amounts in small bowel, colon and pancreas, as well as in breast tissue. The relative levels of constitutive expression in the liver and intestine show little concordance, suggesting that different mechanisms operate in each tissue. While CYP3A4 is constitutively expressed in all adult human livers, there is a 10-fold variability of CYP3A4 mRNA between liver samples. Variability in intestinal expression is even more marked, with >30-fold variation being reported.

In the case of hepatic CYP3A4 expression, using reporter constructs containing the 5'-flanking region of the CYP3A4 gene, the present inventors have demonstrated that liver-specific factors are preferably required to support CYP3A4 transcription. When a liver-derived cell line (HepG2) was compared to a non-liver-derived line (NIH-3T3) for their ability to support transcriptional activation, either in the presence or absence of hPXR, the non-liver-derived cell line was markedly inferior. Clearly, this suggests an optional role for liver-specific transcription factors. However, the present inventors know that HepG2 cells, despite being a human liver-derived cell line, do not constitutively express CYP3A4 in significant amounts. The present inventors have found that an unusual human orphan nuclear receptor, termed the human constitutive and rostane receptor-β (hCAR-β) [5], when cotransfected into HepG2 cells with a CYP3A4 5'-flanking region reporter construct, causes a 6- to 10-fold increase in reporter activity. hCAR-requires no ligand to transactivate regulatory DNA sequences and it's expression is almost entirely restricted to the liver. Experiments performed using deletion constructs show that the response of the CYP3A4 gene to the hCAR-β receptor is dependant on the XREM. Also, as observed for xenobiotic induction with the hPXR, hCAR-β-mediated constitutive expression was observed when the XREM was linked to the minimal thymidine kinase promoter, though at a lower level than observed with the native promoter. Preliminary experiments suggest that there is cooperativity between the XREM and the Prox-ER6 element in hCAR-β-mediated constitutive expression. However, the native promoter alone shows no response to hCAR-β cotransfection.

Results

Cytochrome P450 3A4 (CYP3A4), the predominant P450 expressed in adult human liver, is subject to transcriptional induction by variety of structurally unrelated xenobiotic compounds, including the antibiotic rifampicin. The present inventors have transfected a human liver-derived cell line (HepG2) with various CYP3A4-luciferase reporter gene constructs containing a nested set of 5'-deletions of the CYP3A4 promoter. Rifampicin-inducible transcription of the reporter gene was only observed with the longest construct. Rifampicin treatment of cells transfected with the −13000/+53-luciferase construct resulted in a 3- to 5 fold increase in reporter gene activity. This construct was activated in a dose-dependent manner by rifampicin with maximal induction at 5 µM. A further set of deletion clones were prepared and the responsive region localised to bases −7800 to −7200, approximately. Polymerase chain reaction-generated deletion mutants suggest that rather than being dependent on a short cis-acting element, the rifampicin-response is reliant upon the integrity of larger region encompassing several hundred bases. This region, in conjunction with a minimal CYP3A4 promoter (−362 to +53), was capable of conferring rifampicin-responsiveness on the reporter gene. The induction was independent of the orientation of the −7800/−7200 fragment and its position relative to the proximal promoter of CYP3A4. Heterologous reporter gene constructs, containing the distal enhancer region of CYP3A4 ligated to the herpes simplex virus thymidine kinase promoter, were also capable of inducing luciferase expression following rifampicin treatment. Nucleotide sequence analysis of this region revealed a number of putative transcription factor binding sites. In summary, the present inventors have identified an enhancer region in the CYP3A4 gene capable of mediating transcriptional activation by rifampicin.

Using a series of deletion constructs of the CYP3A4 gene 5'-flanking region, the present inventors have discovered a DNA sequence, lying approximately 7.5 kilobases 5' to the transcription initiation site of the human P450 CYP3A4 gene, that is responsible for the transcriptional induction of the CYP3A4 gene by xenobiotic inducers, including therapeutic drugs. The present inventors have called this element a 'xenobiotic-responsive enhancer module' (XREM). This work has initially performed with the potent CYP3A4 inducer, rifampicin, an antibiotic commonly used to treat tuberculosis. Preliminary studies with other drugs, however, suggest that the XREM may be capable of responding to a broad range of chemical compounds. The present inventors have used the XREM-containing DNA sequence from CYP3A4 to construct cell culture models that respond to xenobiotic inducers by increasing the transcription of the CYP3A4 gene in a manner analogous to that occurring in humans.

The present inventors cotransfected a CYP3A4 5'-flanking region construct, containing the XREM and linked to a luciferase reporter, into HepG2 cells either with or without a hPXR expression construct (pSG-hPXR). The addition of the hPXR substantially increased the transcription rate of the reporter construct, both constitutively (treated with vehicle alone) and following the addition of a xenobiotic inducer (5 µM rifampicin). The observation that addition of the hPXR alone increases the transcription rate of the GYP3A4 XREM-containing reporter indicates that the hPXR is capable of some transactivation in the absence of ligand or that an endogenous ligand for the hPXR exists within the HepG2 cells.

The hPXR has been shown to bind to cis-acting DNA response elements (PXRE) as a heterodimer with the retinoid-x receptor (RXR). The PXRE seems to generally consist of a repeat of the sequence TGAACT, either as direct or everted/inverted repeats. The present inventors have identified a number of putative nuclear receptor response elements (PXREs) within the XREM shown in Table 1.

The present inventors have performed gel mobility shift experiments with $^{32}$P-labelled oligonucleotide probes to determine if hPXR-RXR heterodimers were capable of binding to the putative PXREs within the XREM.

To further examine the contribution of the putative PXREs within the XREM region to the transcriptional induction of CYP3A4 by rifampicin, a series of luciferase reporter constructs containing deletions and/or site-directed mutagenesis of the PXREs were created (FIG. 5). Deletion of the region containing the PXRE XREM-DR3-1 (−7834 to −7610 bp) resulted in almost complete abrogation of transcriptional activity. This was not entirely due to the loss of function of XREM-DR3-1 as site directed mutagenesis of this PXRE resulted in only a 47% loss of activity. Mutation of XREM-DR6 also decreased transcription rate (to 52% of the wild-type) despite the apparent failure of this motif to bind a hPXR-RXR heterodimer in the gel-shift experiment. It is possible that this site binds other transcription factors or is a low-affinity site for hPXR-RXR.

It can be appreciated that the putative PXRE within the proximal promoter region which consists of the Prox-ER6 motif has no function on its own. However, site-directed mutagenesis of the Prox-ER6 in a construct containing the complete XREM does decrease the transcription rate (to 41% of the wild-type) (FIG. 5) suggesting cooperativity between the XREM and Prox-ER6.

Figure 4:
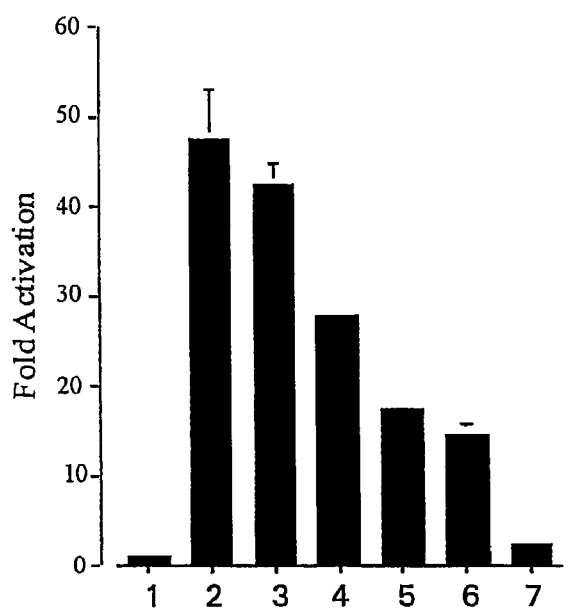
FIG. 4 shows the effect of various inducing drugs on HepG2 cells containing a CYP3A4 XREM reporter construct and a hPXR expression vector compared to vehicle (dimethyl sulphoxide) 0.1% alone. Legend: 1, DMSO; 2, rifampicin; 3, RU-486; 4, clotrimazole; 5, phenobarbital; 6, metyrapone; 7, pregnenalone 16.alpha.-carbonitrile.

The XREM Mediates the Transcriptional Induction of the CYP3A4 Gene to Many Xenobiotics, Not Only Rifampicin Many drugs induce the transcription of the CYP3A4 gene. Because of its potent induction properties, the present inventors used rifampicin to identify and characterise the XREM. To determine if an XREM-containing reporter construct was capable of responding to other xenobiotics, HepG2 cells transfected with the XREM were treated with a range of drugs (FIG. 4). It was found that RU-486 (mifaprostone) and clotrimazole induced the XREM construct in a manner analogous to that that occurs in vivo. The present inventors have also examined a wider range of drugs known to induce CYP3A4 in vivo and found that the in vitro model developed closely reflects in vivo experience.

Uses for the Invention

The invention has several areas of application, including but not restricted to, therapeutic drug development. In some of these areas of application, XREM containing DNA constructs are used to determine the effects of compounds on CYP3A gene transcription. These constructs typically include reporter genes to allow for the convenient measurement of gene activity. Such reporter genes include chloramphenicol acetyl transferase, luciferase, alkaline phosphatase and green fluorescent protein, though any detectable gene product, including messenger RNA (mRNA) could be used. Such gene constructs are introduced transiently or permanently into suitable cultured cells, or as a transgene in transgenic animals. Additional DNA constructs can be cotransfected along with the XREM-containing constructs to provide suitable conditions to answer particular questions regarding CYP3A gene regulation. Such cotransfected constructs include expression plasmids for hPXR and hCAR-β which the present inventors have demonstrated to interact with the XREM. Present studies have also shown that there are many protein-DNA interactions within the XREM so it is likely that other cotransfected constructs will prove useful for certain situations.

Another area of application is the use of the XREM sequence to examine human genomic DNA for the presence of polymorphisms relevant to CYP3A4 gene expression. Such polymorphisms may be linked to several areas of use including the prediction of drug metabolising ability and disease associations.

The Use of Cell or Transgenic Animal Models to Screen Chemical Substances for the Ability to Induce the Formation of the CYP3A4 Enzyme Induction of CYP3A subfamily enzymes by therapeutic drugs is generally considered to be an undesirable effect. Such induction may increase the elimination of the drug itself or co-administered drugs. This generally renders drugs less effective. The ability to screen potential drugs for CYP3A induction during the early development phase is a useful in that such drugs may be discarded in favour of ones that do possess this action. The information gained from such drug screening also allows the development of structure-function relationships, which indicate molecules or parts of molecules that have the propensity to induce CYP3A4. Such knowledge allows the use of rational drug design to synthesize new compounds that have more favourable characteristics. This process can be applied to existing drugs that undesirably induce CYP3As, such as those listed in Table 2.

TABLE 2

A non-exclusive list of therapeutic drugs known to induce the expression of the CYP3A4 gene.

Drug

Carbamazepine
Clotrimazole and other imidazole anti-mycotics
Lovastatin
Phenytoin
Phenobarbitone
Rifampacin
Rifabutin
RU-486

In addition to the above, there are potential therapeutic uses for drugs specifically designed to induce or inhibit CYP3A enzyme formation as their primary action. Inducers of CYP3A4 can be used to accelerate the metabolism of xenobiotic toxins or endogenously produced substances that are CYP3A4 substrates. Inhibitors of CYP3A4 could be used to overcome the undesirable induction of CYP3A4 by therapeutic drugs, such as those listed in Table 2. It will be appreciated that there are many potential uses of drugs specifically designed to modulate CYP3A enzyme formation, other than those listed here. The XREM sequence is useful in identifying such drugs.

The XREM as a Tool for Pharmacogenetic Analysis/Disease Susceptibility

There are marked inter-individual differences in the capacity of humans to metabolise xenobiotic compounds (such as therapeutic drugs) and endogenous compounds (such as endogenously-secreted hormones). At least some of these differences can be related to polymorphisms in the genes encoding the enzymes or transport proteins that interact with these xenobiotic or endogenously produced compounds.

Members of the cytochrome P450 gene superfamily are involved in the metabolism of a large range of lipophilic substrates. CYP3A subfamily P450s (such as CYP3A4) are particularly involved in the metabolism of therapeutic drugs and endogenously produced steroid hormones. It is well recognised that there are marked inter-individual differences in the metabolism of CYP3A substrates (up to 20-fold), however, to date, no polymorphisms within the CYP3A4 protein coding region of the CYP3A4 gene have been found to account for these differences. This strongly suggests that it is the regulation of CYP3A gene expression that accounts for these inter-individual differences.

The present inventors have demonstrated that the XREM region of CYP3A4 is an important regulatory element for the transcriptional control of the expression of this gene. It follows that polymorphisms within the XREM could significantly effect gene transcription and the expression of CYP3A4 protein, thus explaining, at least in part, the inter-individual differences in CYP3A-mediated metabolism.

Rebbeck and colleagues have recently described a polymorphism in the proximal 5'-flanking region of the CYP3A4 gene that correlates with more severe forms of prostate cancer [6] and a reduced incidence of secondary leukaemia following cancer chemotherapy [7]. It is presumed that this polymorphism caused these changes due to effects on CYP3A4 expression though this has yet to be proven.

Thus, use of the XREM sequence and function provides a potentially powerful tool to search for CYP3A gene polymorphisms. Screening for such polymorphisms would be of considerable usefulness in determining the ability of an individual to metabolise drugs (pharmacogenetic analysis) or determine disease susceptibility (eg., prostate cancer). The method for carrying out such screening typically involves the amplification of the genomic DNA region of interest (in this case the XREM) using polymerase chain reaction (PCR). The PCR product can then be examined for polymorphisms using one of several techniques such as restriction fragment length polymorphisms (RFLP), sequencing of DNA or single-stranded conformational polymorphisms (SSCP) of DNA.

The Use of the XREM as an Inducible Enhancer for Gene Expression in the Broader Context of Molecular Biology, Transgenics and Directed Gene Expression The concept of using a portion of a cytochrome P450 gene as a genetic switch has been previously demonstrated using the CYP1A1 gene. As the XREM region of the CYP3A4 gene is capable of regulating transcription in response to xenobiotics as well as certain steroid hormones, it is potentially useful as a genetic switch within the broad context of molecular biology and directed gene expression. An example is the activation of a transgene in the liver of an animal via a PXR/XREM-dependant mechanism.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. Lehmann J M, et al. (1998) The human orphan nuclear receptor PXR is activated by compounds that regulate CYP3A4 gene expression and cause drug interactions J Clin Invest 102:1016-1023.
2. Bertilsson G, at al. (1998) Identification of a human nuclear receptor defines a new pathway for CYP3A induction. Proc Natl Acad Sci USA 95:12208-12213.
3. Blumberg B, et al. (1998) SXR, a novel steroid and xenobiotic sensing receptor. Genes & Dev 12:3195-3205.
4. Mangelsdorf D J, et al. (1995) The nuclear receptor superfamily: the second decade. Cell 83:835-839.
5. Baes M, et al. (1994) A new orphan member of the nuclear hormone receptor superfamily that interacts with a subset of retinoic acid response elements. Mol Cell Biol 14:1544-52.

6. Rebbeck T R, et al. (1998) Modification of the clinical presentation of prostate tumors by a novel genetic variant in CYP3A4. J Natl Cancer Inst 90:1225-1229.

7. Felix C A, et al. (1998) Association of CYP3A4 genotype with treatment-related leukemia. Proc Natl Acad Sci USA 95:13176-81.

The invention claimed is:

1. An isolated nucleic acid molecule comprising a nucleotide sequence forming a transcriptional enhancer of cytochrome P450 CYP3A4 production or expression, the nucleic acid including each of the following nuclear receptor response elements from the 5'-flanking region of CYP3A4: TGAACT(n)$_3$TGACCC (SEQ ID. NO. 8), TGAAAT(n)$_6$GGTTCA (SEQ ID. NO. 9), TGAATC(n)$_6$TGAACT (SEQ ID. NO. 10) and TATTGT(n)₃TGAACT (SEQ ID. NO. 11), wherein n is adenine (A), guanine (G), thymine (T) or cytosine (C) and further including a nucleotide sequence encoding a reporter molecule for indicating regulation of transcription of the reporter nucleotide sequence by the nucleotide sequence forming a transcriptional enhancer of cytochrome P450 CYP3A4 production or expression.

2. An isolated nucleic acid molecule according to claim 1, wherein the reporter molecule is selected from the group consisting of: firefly luciferase, beta-galactosidase, alkaline phosphatise, green fluorescent protein or chloramphenicol acetyl transferase.

3. A vector comprising a nucleic acid molecule according to claim 1.

4. A vector comprising a nucleic acid molecule according to claim 2.

5. An isolated cell comprising a vector according to claim 3 or claim 4.

6. An isolated cell comprising the vector according to claim 3 or claim 4, further comprising a nucleic acid molecule encoding the pregnane-X-receptor (PXR).

7. An isolated cell comprising the vector according to claim 3 or 4, further comprising a nucleic acid molecule encoding the human constitutive androstane receptor-β (hCAR-β).

* * * * *